United States Patent [19]

Jaffe

[11] Patent Number: 5,193,544
[45] Date of Patent: Mar. 16, 1993

[54] SYSTEM FOR CONVEYING GASES FROM AND TO A SUBJECT'S TRACHEA AND FOR MEASURING PHYSIOLOGICAL PARAMETERS IN VIVO

[75] Inventor: Richard A. Jaffe, Palo Alto, Calif.

[73] Assignee: Board of Trustees of the Leland Stanford Junior University, Stanford, Calif.

[21] Appl. No.: 650,824

[22] Filed: Jan. 31, 1991

[51] Int. Cl.$^5$ .................. A61B 5/00; A61M 16/04
[52] U.S. Cl. .................. 128/634; 128/207.14
[58] Field of Search .............. 128/633, 634, 664, 665, 128/713, 207.15, 207.16, 716, 719, 207.14

[56] References Cited

U.S. PATENT DOCUMENTS

| | | |
|---|---|---|
| 3,998,550 | 12/1976 | Konishi et al. . |
| 4,170,997 | 10/1979 | Pinnow et al. . |
| 4,176,660 | 12/1979 | Mylrea et al. . |
| 4,223,680 | 9/1980 | Jobsis . |
| 4,281,645 | 8/1981 | Jobsis . |
| 4,337,761 | 7/1982 | Upsher . |
| 4,383,534 | 5/1983 | Peters . |
| 4,444,185 | 4/1984 | Shugar . |
| 4,537,190 | 8/1985 | Caillot et al. . |
| 4,565,194 | 1/1986 | Weerda et al. . |
| 4,567,882 | 2/1986 | Heller ........................ 128/11 |
| 4,584,998 | 4/1986 | McGrail . |
| 4,648,396 | 3/1987 | Raemer . |
| 4,691,701 | 9/1987 | Williams . |
| 4,728,499 | 3/1988 | Fedher . |
| 4,730,622 | 3/1988 | Cohen . |
| 4,738,266 | 4/1988 | Thatcher . |
| 4,742,819 | 5/1988 | George . |
| 4,750,495 | 6/1988 | Moore . |
| 4,800,886 | 1/1989 | Nestor . |
| 4,809,706 | 3/1989 | Watson et al. . |
| 4,819,752 | 4/1989 | Zelin . |
| 4,859,057 | 8/1989 | Taylor et al. . |
| 4,903,701 | 2/1990 | Moore et al. . |
| 4,907,594 | 3/1990 | Muz . |
| 5,005,573 | 4/1991 | Buchanan ...................... 128/207.14 |

Primary Examiner—Lee S. Cohen
Assistant Examiner—Kevin Pontius
Attorney, Agent, or Firm—Majestic, Parsons, Siebert & Hsue

[57] ABSTRACT

An optical path is provided in the wall of an endotracheal tube to transmit light from a light source to the tracheal tissue. The same path or different path may be used to receive light reflected from the tracheal tissue to a detector for detecting the oxygen saturation of blood of a subject. The light supplied may also be directed across the gaseous medium inside the tube and received by a different optical path. The received light signal is then detected to determine the carbon dioxide concentration of the medium inside the trachea.

15 Claims, 3 Drawing Sheets

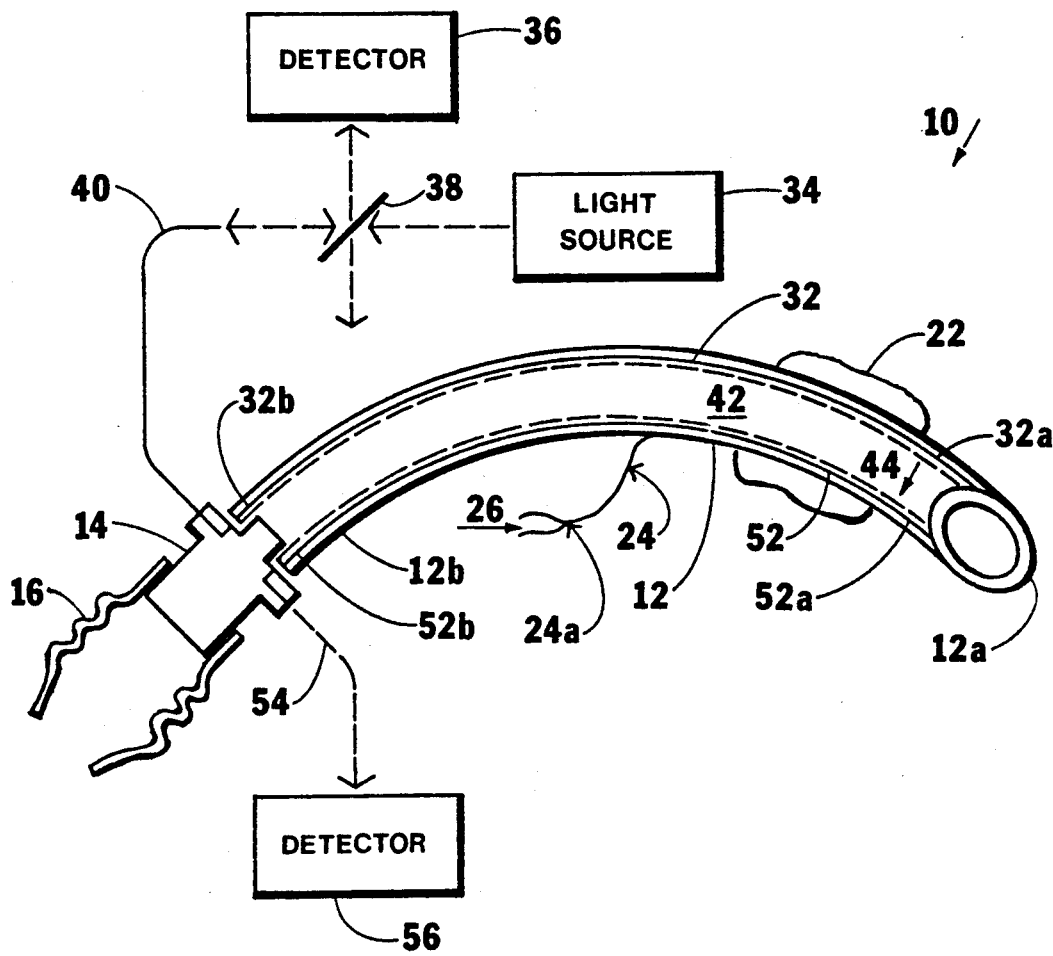
FIG.—1.
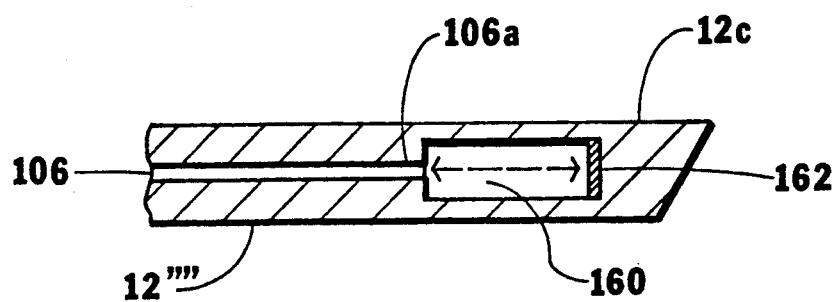
FIG.—6.

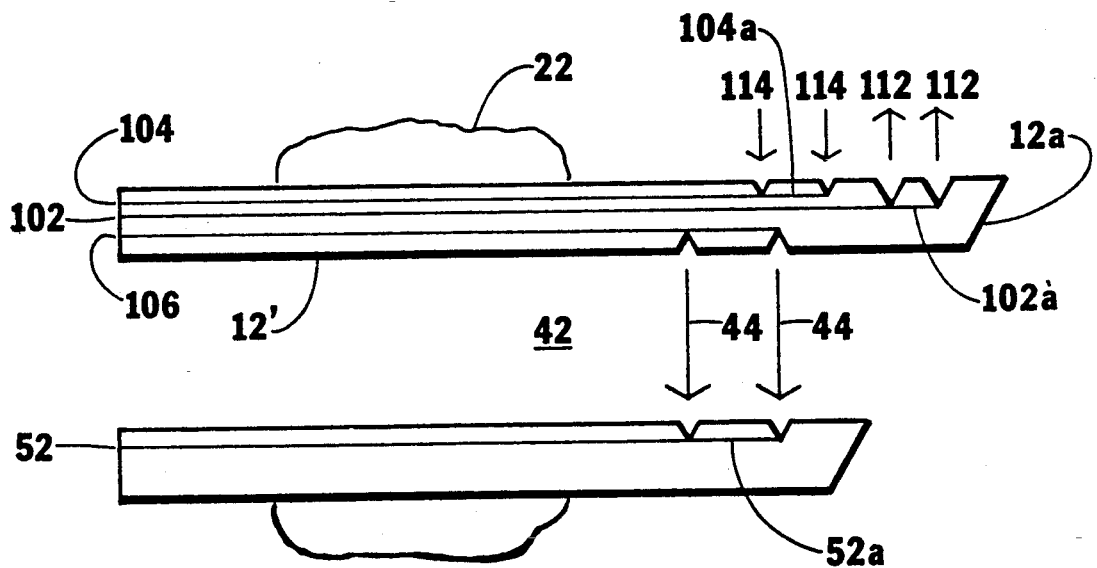
FIG.—2.
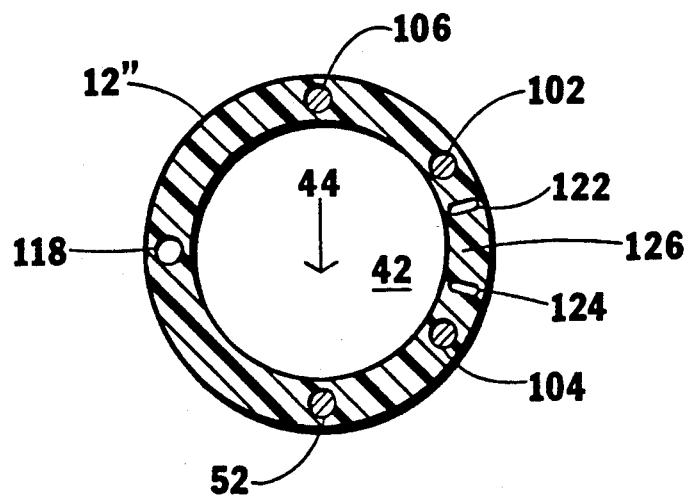
FIG.—3.

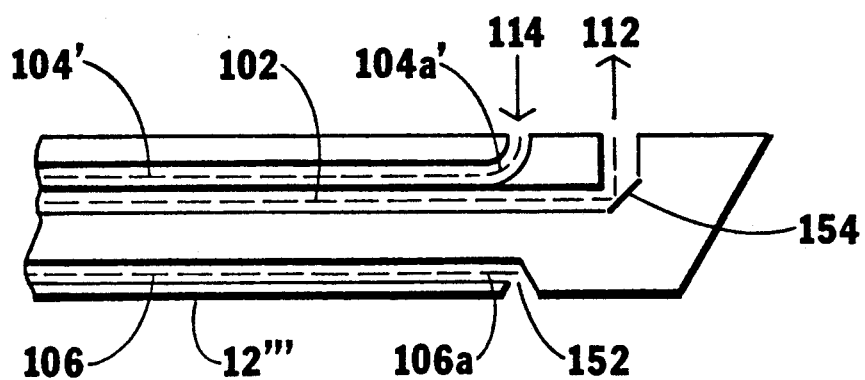
FIG._4.
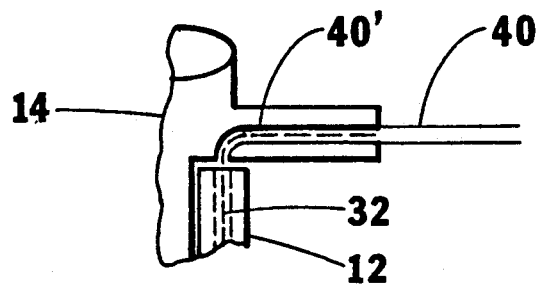
FIG._5.

SYSTEM FOR CONVEYING GASES FROM AND TO A SUBJECT'S TRACHEA AND FOR MEASURING PHYSIOLOGICAL PARAMETERS IN VIVO

BACKGROUND OF THE INVENTION

This invention relates to a system for conveying gases from and to a subject's trachea and for measuring physiological parameters in vivo.

In many medical settings, such as when a human or animal subject is under anesthesia, it is necessary to monitor various physiological parameters of the subject, such as oxygen saturation in the blood and end-tidal carbon dioxide of the subject. In accordance with conventional methods for monitoring such physical parameters, oxygen saturation in the blood is measured by pulse oximetry at the limbs of the subject, such as at fingertips or toes. Infrared light or light in the red region is directed at the fingers or toes of the subject and the reflected light measured to determine the percentage content of oxygen contained in the blood by comparing the absorption of light in the infrared region to absorption of light in the red region. Typically, a light source such as a light-emitting diode emits light which is directed towards the monitoring site and a photodiode-type detector is used for detecting the light transmitted through the blood vessels present at the monitoring site. The blood vessels of such extremities such as toes or fingertips of a subject would sometimes constrict because of the effects of a cold environment, fear or stress on the subject. When this happens, the amount of blood profusing in the blood vessels at these peripheral monitoring sites is significantly reduced which in turn reduces the accuracy of the measurement. It is therefore desirable to provide an improved system for monitoring oxygen saturation of subjects.

In order to monitor the end-tidal carbon dioxide of a subject, the respired gases are connected from the subject through a tube to a chamber in monitoring equipment which monitors the carbon dioxide concentration in the chamber. As is known to those skilled in the art, the end-tidal carbon dioxide concentration is an important physiological parameter. In the above-described conventional monitoring technique, the dead space volume in the connecting tube and the chamber of the monitoring equipment can cause the end-tidal carbon dioxide to be diluted by the gases already present in the tube and the chamber, thereby reducing the accuracy of the measurement. This is particularly true for weak subjects such as infants or seriously ill subjects. Furthermore, it will be difficult to distinguish between the end-tidal carbon dioxide and the carbon dioxide exhaled by the subject before the end-tidal point is reached. It is therefore desirable to provide an improved technique for monitoring the end-tidal carbon dioxide concentration.

SUMMARY OF THE INVENTION

In many medical situations, a human or animal subject would require assistance in breathing. In such event, an endotracheal tube is inserted into the trachea of the subject either through the nose or the mouth, where the end of the tube inside the trachea is referred to below as the subject end and the other end of the tube is often connected to a respirator to assist the subject in breathing. This invention is based on the observation that physiological parameters of the subject may be measured in vivo by providing an optical path in the wall or lumen of the endotracheal tube between a location of the tube inside the trachea and a portion of the tube outside the subject. Light is then provided from a light source to the end of the path external to the subject so that the light provided will travel through the path to illuminate the tracheal mucosa. The same or different optical path is then used to collect the light reflected from the tracheal tissue and transmit such received light to an external detector in order to measure the oxygen saturation in the blood of the subject.

In addition to or instead of illuminating tracheal tissue, light carried by the optical path originating from the light source may also be directed across the gases present inside the endotracheal tube inside the trachea towards another optical path for transmission to a detector in order to measure end-tidal carbon dioxide concentration.

The apparatus of this invention conveys gases from and to a subject's trachea and measures a physiological parameter in vivo. The apparatus comprises a tube suitable for insertion into the trachea and for conveying gases, at least one light source, at least one light detector, and at least one optical path along the tube and having two ends. The path is suitable for passage of light signals between the trachea or locations within the trachea at one end of the path and a light source and/or detector at the other end for measuring the physiological parameter of the subject.

The method of this invention employs the apparatus described above. The method includes the step of providing light to the external end of the optical path to illuminate a portion of the trachea or locations within a medium within the trachea and the step of measuring light reflected from the trachea or transmitted through the medium in the tube in order to measure a physiological parameter of the subject.

BRIEF DESCRIPTION OF THE DRAWINGS

FIG. 1 is a schematic view of a system for conveying gases from and to a subject's trachea and for measuring physiological parameters in vivo to illustrate an embodiment of the invention. The system includes an endotracheal tube for conveying the gases and means for measuring physiological parameters.

FIG. 2 is a saggital section view of a section of the endotracheal tube with optical paths for measuring physiological parameters to illustrate an alternative embodiment of the invention.

FIG. 3 is a cross-sectional view of an endotracheal tube to illustrate the invention.

FIG. 4 is a cross-sectional view of a portion of the endotracheal tube useful for the system of FIG. 1 to illustrate the invention.

FIG. 5 is a schematic view of an optical connector and of an endotracheal tube to illustrate the invention.

FIG. 6 is a cross-sectional view of a portion of an endotracheal tube to illustrate a second alternative embodiment of the invention.

DETAILED DESCRIPTION OF THE INVENTION

FIG. 1 is a schematic view of a system for conveying gases from and to a subject's trachea and for measuring physiological parameters in vivo to illustrate an embodiment of the invention. System 10 of FIG. 1 includes an endotracheal tube 12 and a connector 14 connecting tube 12 to another tube 16 of a respirator (not shown). End 12a of tube 12 is suitable to be inserted into the trachea of a human or animal subject and end 12b is adapted to be connected to connector 14. Oxygen or air is then supplied through tube 16, connector 14 and tube 12 to the trachea of the subject and respired gases are allowed to escape through tube 12, connector 14 and tube 16 in the reverse direction in order to assist respiration of the subject. In such manner, system 10 forms a part of the medical support equipment for assisting the respiration of the subject during medial procedures, such as when the subject is anesthetized.

End 12a, being the end of the tube which is inserted into the subject, is referred to below as the subject end. Cuff 22 is an inflatable sleeve near the subject end of the tube. Cuff 22 provides a leak-resistant fit between the tube and the trachea (not shown) to prevent aspiration of stomach contents, saliva and blood through the tube and allows positive pressure to be applied to the lungs. The cuff also serves to center the tube in the trachea. In order to inflate cuff 22, a small inflating tube 24 with an input end 24a is attached to the wall or lumen of tube 12 and a small passage within the wall or lumen is provided between tube 24 and cuff 22. In such manner, cuff 22 may be inflated by injecting a gas or liquid along direction 26 to the free end 24a of the inflating tube after end 12a has been inserted into the trachea of the subject and tube 12 is in place in the trachea. The function of tube 12 described above up to this point is essentially the same as conventional endotracheal tubes.

As indicated above, in many medical situations such as when the subject is being anesthetized, it is necessary to monitor the oxygen saturation of the subject's blood. In conventional medical technology, this is done by performing pulse oximetry at the blood vessels at an external limb of the subject, such as at its fingers or toes. Such vessels may contract in a phenomenon known as peripheral vascular constriction with reduced flow, thereby causing inaccuracies in the measurement. Such difficulties may be avoided by modifying the conventional endotracheal tube to incorporate one or more optical paths in the manner shown in FIG. 1.

As shown in FIG. 1, the wall or lumen of tube 12 includes an optical path 32 with a first end 32a and a second end 32b. End 32b is connected to a light source 34 and a detector 36 through a beam splitter 38 and optical path 40, where path 40 is connected optically to end 32b at one end through connector 14 and beam splitter 38 at the other as shown in FIG. 1.

To measure the oxygen saturation in the subject's blood, the light source 34 provides light in the infrared and the red regions to path 40 through a beam splitter 38. The light provided travels through path 40 and path 32. When such light reaches end 32a of path 32, the light is emitted at such end to illuminate the tracheal mucosa. Light reflected from the tracheal mucosa is received at end 32a and travels in the reverse direction towards end 32b, path 40 and is reflected by beam splitter 38 towards the detector 36. The detector 36 detects the relative intensities of the reflected light in the infrared and red regions in order to determine oxygen saturation in the blood in the tracheal tissue, a highly profused tissue not subject to peripheral vascular constriction.

System 10 may also be used to monitor the end-tidal carbon dioxide concentration. The respired gases from the trachea of the subject pass through chamber or lumen 42 inside tube 12 before the gases escape through connector 14 and tube 16 to the respirator. Light emitted from end 32a of optical path 32 passes through the medium in chamber 42 along direction 44 and is collected by end 52a of a second optical path 52 also provided in the wall or lumen of tube 12. Conveniently, end 52a may be located on the opposite side of the tube 12 from end 32a. The light so received passes to the other end 52b of the second optical path and is connected by yet another optical path 54 to a second detector 56. By comparing the intensity of light at appropriate frequencies detected by detector 56 to the light provided by light source 34, the concentration of the carbon dioxide in chamber 42 along path 44 may be determined. In such manner, both the oxygen saturation of the blood of the subject and the carbon dioxide and the other gas concentrations in the respired gases of the subject, including the end-tidal carbon dioxide concentration, may be determined.

FIG. 2 is a saggital section view of a portion of the subject end of the endotracheal tube of the type similar to that shown in FIG. 1 but with additional optical paths to illustrate an alternative embodiment of the invention. To simplify the discussion, identical components in the different figures of this application are identified by the same numerals. As shown in FIG. 2, tube 12' differs from tube 12 of FIG. 1 in that tube 12' includes four optical paths 102, 104, 106 and 52 instead of only two optical paths (32, 52) in tube 12 of FIG. 1. As shown in FIG. 2, optical path 102 supplies light from light source 34 to end 102a where it is emitted along direction 112 to illuminate the tracheal mucosa (not shown). The light reflected by the mucosa travels along a number of directions including direction 114. The light reflected along direction 114 is received by end 104a of path 104 which transmits the light to the detector 36. Since the light path from light source 34 and travelling along path 102 in the input direction and the reflected light traveling through path 104 towards the detector 36 in the output direction travel along different paths, a beam splitter such as splitter 38 in FIG. 1 is no longer necessary and path 102 may be connected directly to light source 34 and path 104 directly to detector 36.

Path 106 conveys light from the same source 34 or a different light source than that providing light to path 102. The light so conveyed by path 106 is emitted at end 106a along path 44. The light so emitted thus travels through the medium in chamber 42 towards end 52a of path 52 which is provided through path 54 to detector 56 as described above in reference to FIG. 1. The embodiment in FIG. 2 has the advantage that the light used for detecting carbon dioxide through path 106 may originate from a light source different from that providing light to path 102 for detecting oxygen saturation so that the wavelengths of light provided for the two measurements may be different to optimize the accuracy of each measurement.

The construction of the optical paths in tubes 12, 12' in FIGS. 1 and 2 is now illustrated in reference to FIG. 3. As shown in FIG. 3, optical paths 102, 104, 106 and 52 are optical fibers. Channel 118 is provided to convey gas from the inflation tube 24 of FIG. 1 to cuff 22. Since many endotracheal tubes now on the market are made of a transparent material, a section of the tube itself may be used as an optical path as illustrated in FIG. 3. Thus light barriers 122, 124 define a section of the tube 126 which is optically segregated from the remainder of the tube 12''; such section 126 serves as an optical path which may be used to convey light for the different applications described above. Section 126 may be made of any light conducting material as long as its index of refraction is greater than that of medium 42 (such as nitrogen, carbon dioxide and oxygen) and the medium outside tube 12" (such as a mixture of nitrogen, carbon dioxide, oxygen and water). It is believed that section 126 may be made of a transparent plastic such as an acrylic polymer, for example, although other materials, such as polyethylene and PVC may also be suitable.

FIG. 4 is a cross-sectional view of a portion of an endotracheal tube having optical paths 102, 104, 106 with mechanisms for coupling the ends 102a, 104a, 106a of these paths to the surrounding media. As shown in FIG. 4, end 106a of the path 106 is coupled to chamber 42 through a prism 152 which could be intrinsic to the tube. Light carried by path 102 is reflected by mirror or mirrored surface 154 along direction 112 in order to illuminate the tracheal mucosa. End 104a' is bent towards the surface of the tube 12''' so as to receive light reflected in direction 114 for transmission to a detector. While in FIG. 4, prism 152 and mirror 154 are used to couple light carried by paths 102, 106 to the environment in an emission process, prism 152 and mirror 154 may also be used for receiving light traveling towards the prism and mirror for transmission to detectors 36, 56. Similarly, the bent end 104a' may also be used for emitting light carried by path 104'. In FIG. 4, the three optical paths 102, 104' and 106 are optical fibers where the cladding of the fibers are shown as lines parallel to the fiberoptic core.

FIG. 5 is a schematic view of a portion of the connector 14 and tube 12 of FIG. 1 to illustrate the invention. In order to couple optical path 32 to optical path 40, an optical path 40' is provided in the flange of connector 14 as shown in FIG. 5. In the preferred embodiment, it is preferable to incorporate a unitary path such as an optical fiber for both paths 40 and 40'. For example, a single optical fiber may be embedded in the material of connector 14 in the process of making the connector so that optical paths 40', 40 are formed by a single optical fiber to reduce optical losses in the connection between path 40' and path 40.

To improve the accuracy of measurement, it is often desirable to measure carbon dioxide concentration in the trachea where the carbon dioxide is free of water vapor. This is accomplished by using an endotracheal tube 12''''', a saggital section of a portion which is shown in FIG. 6. As shown in FIG. 6, tube 12'''' has an end portion 12c which is made of a gas-permeable but water impermeant material defining a micro-chamber 160 therein. Thus gas in the trachea diffuses into the microchamber but water is excluded from the chamber. Fiber 106 transmits light from a light source providing light in the infrared region. Such light is emitted from end 106a, travels through the gases in chamber 160 towards mirror 162, is reflected by the mirror and travels back through the gases in chamber 160, and then through path 106 to a detector. Since a single path carries both the light supplied by the light source and the returning light signal destined for the detector, a beam splitter arrangement such as that shown in FIG. 1 may be used to divert the returning light signal towards the detector and away from the light source.

Occasionally, the light transmitted through the endotracheal tube may be blocked by opaque material accumulating in the tube. If the opaque material is stuck at a location that would block the light path permanently, the photodetector would be incapable of performing the function described above. For this reason, it may be desirable to transmit and detect the light at a number of locations along tube 12 instead of at just one location. Thus in reference to FIG. 2, a plurality of paths 52 are employed with a plurality of ends 52a where the ends are arranged along a line or in a two-dimensional array in the wall of tube 12. Such plurality of paths will carry light detected at such plurality of ends 52a to converge on the photodetector. Similarly, a plurality of optical paths 106 with ends spread along a line or in a two-dimensional array in the wall of tube 12 may be employed for transmitting light across the lumen 42 of the tube. It may also be desirable to employ a plurality of optical paths 102a, 104a for carrying light which is to be transmitted to and rejected from the tracheal mucosa.

While the invention has been described by reference to the various embodiments described above, it will be understood that various modifications may be made without departing from the scope of the invention. Thus while the invention above has been described using light in the infrared and red regions, it will be understood that light of other wavelengths may also be used, such as ultraviolet light. The detectors used may be of any suitable type such as photodiodes. All such variations are within the scope of the invention. The invention is to be limited only by the scope of the appended claims.

What is claimed is:

1. An apparatus for conveying gases from and to a subject's trachea and for enabling the measurement of a physiological parameter in vivo or the measurement of respired gas concentrations, comprising:

a tube suitable for insertion into the trachea and for conveying gases;

at least one light source;

at least one light detector; and means for conveying light from the light source to the trachea or locations within the trachea and for conveying light to the light detector from the trachea or locations within the trachea, said light conveying means including at least one optical path having two ends along the tube for passage of light signals between the trachea or locations within the trachea at one end of the path, and the detector at the other end, the at least one optical path transmitting light from the trachea or locations within the trachea along the tube to the detector for enabling the measurement of the physiological parameter or the measurement of respired gas concentrations of the subject.

2. The apparatus of claim 1, said apparatus comprising at least two optical paths, one transmitting light from the light source to the trachea or a location within the trachea and the other path transmitting light from the trachea or a location within the trachea to the detector.

3. The apparatus of claim 1, said apparatus comprising at least two optical paths, one path transmitting infrared light for the measurement of gas concentration in the tube, and the other path transmitting light in the infrared and the red regions of light wavelengths for the measurement of oxygen saturation of blood in trachea tissue.

4. The apparatus of claim 1, wherein said at least one optical path forms part of the tube.

5. The apparatus of claim 1, wherein said at least one optical path is an optical fiber.

6. The apparatus of claim 1, said tube being elongated and having a length, wherein said tube has two light barrier portions and a light transmitting portion between said barrier portions, all three portions being along the length of the tube, said light transmitting portion being the optical path.

7. The apparatus of claim 1, said apparatus comprising at least two optical paths, a first path having an output end and transmitting light from the source to said output end and through said output end to gases within the tube, and a second path having an input end for receiving light that has passed through said gases from the output end, said second path transmitting said received light to the detector for measuring carbon dioxide concentration in the tube.

8. The apparatus of claim 7, said tube being annular, wherein said output and input ends are located on opposite sides of the tube.

9. The apparatus of claim 1, said at least one optical path having a subject end for transmitting light to the trachea or locations within it or for receiving light from the trachea or locations within it for transmission to the detector, said subject end including a curved path terminating at a surface of the tube.

10. The apparatus of claim 1, said at least one optical path having a subject end for transmitting light to the trachea or locations within it or for receiving light from the trachea or locations within it for transmission to the detector, said subject end including a prism or reflecting surface for transmission or reception of light to or from the trachea or locations in the trachea.

11. The apparatus of claim 1, wherein the light conveying means further comprises a connector connecting the tube to medical equipment, said connector having an additional optical path positioned to transmit light between the at least one optical path and the detector or the light source.

12. The apparatus of claim 1, wherein said light source provides ultraviolet light to the at least one optical path.

13. The apparatus of claim 1, wherein said light source provides light in the infrared and the red regions to the at least one optical path.

14. A method for measuring data useful for determining a physiological parameter or the respired gas concentrations of a subject employing a tube suitable for insertion into the trachea of the subject, said trachea having a medium therein, said tube having at least one optical path having a first and a second end along the tube for passage of light signals between the trachea or locations within the trachea at the first end of the path and the second end of the path, said method comprising:
providing light to illuminate a portion of the trachea or locations within the medium; and
measuring light reflected from the trachea or transmitted through the medium in the tube, said reflected light indicative of a physiological parameter or of the respired gas concentrations of the subject.

15. The method of claim 14 further comprising, prior to the measuring step, transmitting light reflected from the trachea or transmitted through the medium in the tube through the path from the first to the second end.

* * * * *